United States Patent
Bourdon

[11] Patent Number: 5,664,562
[45] Date of Patent: Sep. 9, 1997

[54] BREATHING AID DEVICE

[75] Inventor: Guy Bourdon, Verrieres le Buisson, France

[73] Assignee: Pierre Medical S.A., France

[21] Appl. No.: 403,684

[22] PCT Filed: Sep. 17, 1993

[86] PCT No.: PCT/FR93/00902

§ 371 Date: Mar. 13, 1995

§ 102(e) Date: Mar. 13, 1995

[87] PCT Pub. No.: WO94/06499

PCT Pub. Date: Mar. 31, 1994

[30] Foreign Application Priority Data

Sep. 18, 1992 [FR] France ................... 92 11131

[51] Int. Cl.$^6$ .................................................. A61M 16/00
[52] U.S. Cl. .............................. 128/204.23; 128/204.18; 128/204.21; 128/205.24; 128/205.25
[58] Field of Search ..................... 128/204.18, 204.21, 128/204.23, 204.26, 205.13, 205.18, 205.24, 205.25

[56] References Cited

U.S. PATENT DOCUMENTS

| | | | |
|---|---|---|---|
| Re. 32,553 | 12/1987 | Bennett et al. | 137/271 |
| 3,985,131 | 10/1976 | Buck et al. | 128/204.23 |
| 4,239,039 | 12/1980 | Thompson | 128/205.24 |
| 4,249,528 | 2/1981 | Mathes | 128/205.13 |
| 4,281,651 | 8/1981 | Cox | 128/204.23 |
| 4,401,115 | 8/1983 | Monnier | 128/204.23 |
| 4,421,113 | 12/1983 | Gedeon et al. | 128/204.23 |
| 4,466,433 | 8/1984 | Robbins | 128/202.22 |
| 4,686,975 | 8/1987 | Naimon et al. | 128/204.23 |
| 4,712,580 | 12/1987 | Gillman et al. | 137/512.15 |
| 5,000,173 | 3/1991 | Zalkin et al. | 128/204.21 |
| 5,072,729 | 12/1991 | DeVries | 128/204.23 |
| 5,134,995 | 8/1992 | Gruenke et al. | 128/204.23 |
| 5,148,802 | 9/1992 | Sanders et al. | 128/204.18 |

OTHER PUBLICATIONS

Walter Jager, "Microprocessor Based Disconnect Monitor in Surgery," UBC Engineer, Spring, 1982, pp. 28–31.

*Primary Examiner*—V. Millin
*Assistant Examiner*—William J. Deane, Jr.
*Attorney, Agent, or Firm*—Bierman, Muserlian and Lucas, LLP

[57] ABSTRACT

A patient circuit (1) comprises an inspiratory branch (3) connected to an inspiratory flow rate source (11), and an expiratory branch (4) connected to the atmosphere through an expiratory valve ($V_E$). An inspiratory valve ($V_I$) is arranged between the inspiratory flow rate source (11) and the inspiratory branch (3). During inspiration, the inspiration valve ($V_I$) is open and the pressure of the inspiratory flow source is applied to the expiration valve ($V_I$) to close the latter. During expiration, the inspiration valve ($V_I$) is closed, and the control inlet (6) for controlling the expiration valve ($V_I$) is connected through a control valve (VC1) to a low pressure source (14) adjustable in a range including the zero value. The patient breathes as desired under atmospheric pressure or under positive expiratory pressure. Utilization for making a simple apparatus which provides for multiple adjustments, and compatible with its utilization at home.

68 Claims, 5 Drawing Sheets

BREATHING AID DEVICE

DESCRIPTION

The present invention relates to a breathing aid device, also called "ventilation device" or "ventilator".

Ventilation through inspiratory aid is a partial ventilation mode well known in resuscitation.

In the following, the respiratory exchanges brought about and/or assisted by an apparatus are called "ventilation". Channelling elements, such as a mask, a duct etc., which connect the patient's airways to the means for producing the gaseous flow in the breathing aid apparatus will be called the "patient circuit". The apparatuses covered by the invention are intended to aid, by means of a slight overpressure upon inspiration, those patients who, while suffering from respiratory difficulties, nevertheless retain a respiratory activity and a respiratory timing which are to be respected.

Inspiratory aid involves the application during the inspiratory phase, initiated in principle by the patient, of a constant positive pressure in the patient circuit of a respiratory apparatus.

In apparatuses for ventilation through inspiratory aid, expiration, likewise initiated by the patient, is passive and takes place at atmospheric pressure or under a positive expiratory pressure, also called PEP.

The ventilators used in resuscitation are complex machines, comprising several modes of ventilation, operating on the basis of compressed gases which are suited to intubed or tracheotomized patients, i.e. those provided with a breathing cannula introduced into the trachea artery through the nose or respectively through an incision in the neck.

Known according to EP-B-317417 is a breathing aid device in which the patient circuit comprises a pneumatically controlled expiration valve. During the inspiration phase, the control inlet of this valve is subjected to the pressure from a pressurized flow source, which closes the expiration valve and consequently connects the patient circuit to the pressurized flow source in a leak-tight manner. When a significant reduction in the inspired flow is detected, an electronic control device interrupts the operation of the pressurized flow source, the structure of which is such that its outlet orifice then finds itself returned to atmospheric pressure. This pressure is thus applied to the expiration valve, which allows the latter to open.

This device can operate only under expiratory pressure equal to atmospheric pressure.

Also known according to EP-A-0425092 is a breathing aid device comprising, instead of the expiration valve, a calibrated permanent leak orifice, while the pressure of a flow source is regulated at two different levels, according to whether one finds oneself in inspiration or expiration phase.

This device can operate only under positive expiration pressure, in such a way that the direction of the flow between the flow source and the patient is always oriented towards the patient, even during the expiration phases, in order to prevent expiratory gas from rising towards the flow source during the expiratory phases, to be reinspired at the time of the following inspiratory phase.

Also known, according to FR-A-2 291 739, EP-A-0 042 321, are volumetric apparatuses imposing on the patient the respiratory volumes and timing for patients who no longer have a respiratory reflex.

FR-A-1 492 136 also imposes the timing of breathing on him.

U.S. Pat. No. 4,838,257 controls, in an analogous manner, the wave forms imposed on the patient.

The first three of these documents describe a distribution valve arranged in the inspiration circuit and controlled so as to be closed during expiration. However, this is a valve driven according to parameters peculiar to the breathing apparatus itself so as to require a patient in a comatose state to breathe according to a determined cycle and with determined volumes.

The object of the invention is thus to propose a breathing aid device the basic structure of which is as compatible with expiration under atmospheric pressure as with expiration under positive expiratory pressure, while at the same time being relatively economical and compact, to be suitable in particular for operation in the patient's home.

According to the invention, the breathing aid device comprises a patient circuit having an inspiratory branch connected to a pressurized inspiratory flow source and an expiratory branch in which is installed an expiration valve which is controlled so as to be closed during inspiration, the device also comprising driving means connected to at least one sensor detecting the respiratory activity of the patient and distribution means which in inspiratory phase establish the communication between the inspiratory flow source and the inspiratory branch of the patient circuit, and in expiratory phase interrupt this communication at least partially, characterized in that the distribution means are controlled by the driving means, which control the interruption of the said communication when the sensor detects that the patient is preparing an expiratory phase, and in that the driving means also control, a least indirectly, the expiration valve in order that it determines a predefined expiratory pressure substantially independent of the operating state of the inspiratory flow source.

According to the invention, the inspiratory flow source of the aid apparatus is no longer controlled in order to make it operate in a particular manner when the patient is breathing out, but an interruption of the communication between the inspiratory flow source and the patient circuit is controlled, and the expiration pressure is adjusted by means which are independent of the operating state of the inspiratory flow source. What is novel about this interruption of communication, even compared with forced-breathing apparatuses, is that it is controlled principally by the respiratory activity of the patient, while the means for controlling the apparatus act only as relays.

The interruption of communication between the inspiratory flow source and the inspiratory branch during expiration prevents the inspiratory branch from accumulating the expired gases. This removes the risk of large quantities of expired gas then being reinhaled. Therefore account no longer needs to be taken of the problem of reinhalation in order to define the pressure to which the patient is subjected during expiration.

In addition, the separation between the control of the expiration valve and the operating state of the inspiratory flow source during the expiratory phases allows the expiratory pressure to be defined without any longer having to take account of the operating requirements of the inspiratory flow source. As a result, the invention permits a free choice of expiratory pressure.

The notion of independence between the expiration pressure defined by the expiration valve and the operating state of the inspiratory flow source must be assessed in a relative manner, and in particular in view of the state of the art. According to EP-B-317417, one is obliged to modify the operation of the inspiratory flow source in order that the expiration valve modifies its operation at the time of the transitions between the respiratory phases.

On the contrary, according to the invention, one is freed from this constraining relationship. However, this does not exclude, for example, the possibility that the expiration valve is of the pneumatically controlled type, and is controlled by a pressure source realized from a calibrated loop connected to the outlet of the inspiratory flow source, as will be seen in an example described later. In this non-limitative case, the calibration creates independence, since the calibration can be chosen in order that the expiration valve ensures the desired expiratory pressure.

The inspiratory flow source is preferably a source whose flow aims to cancel itself when the pressure at its outlet assumes a maximum value which is of the order of magnitude of an inspiration aid pressure.

Thus, when during an expiratory phase the distribution means interrupt, at least partially, the communication between the inspiratory flow source and the inspiratory branch of the patient circuit, the inspiratory flow source does not require particular driving: it continues to operate at zero flow, with merely a slight increase in its pressure.

It is advantageous that, as mentioned above, the expiration valve is of the pneumatically controlled type. In order that it determines the expiratory pressure, the driving means connect its control inlet to a low pressure source. The latter may comprise a link between the outlet of a second flow source and an exhaust nozzle. The adjustment of the flow of this second flow source permits the adjustment of the pressure applied to the control inlet of the expiration valve and as a result permits the adjustment of the pressure under which the patient will have to breathe out in order to be able to bring about the opening of the expiration valve. If the flow of the second flow source is adjusted to zero value, the control inlet is in communication with the atmosphere via the exhaust nozzle and as a result the expiratory pressure is equal to the atmospheric pressure.

Other particular features and advantages of the invention will emerge from the following description, relating to non-limitative examples.

Figure 1:
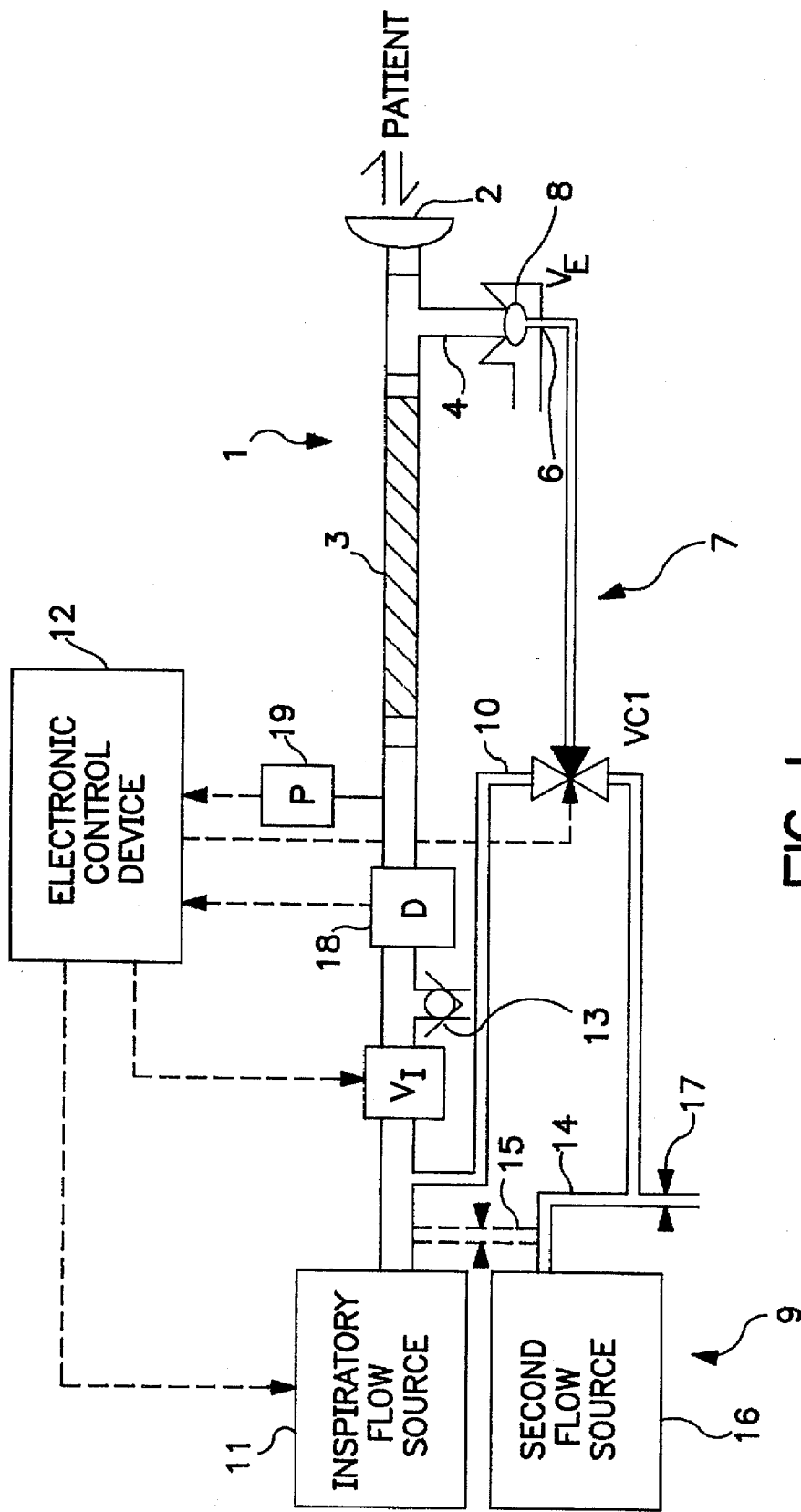
FIG. 1 is a diagram of a first embodiment of the device according to the invention.

In the example represented in FIG. 1, the breathing aid device comprises a patient circuit 1 which in turn comprises a facial, nasal or buccal mask 2, connected to an inspiratory branch 3 and to an expiratory branch 4. The expiratory branch 4 comprises an expiration valve $V_E$ of the pneumatically controlled type comprising a control inlet 6 connected to a control circuit 7.

The expiration valve $V_E$ comprises a cut-off device 8 which closes the valve if the relative pressure at the control inlet 6 is at least equal to a predetermined fraction of the relative pressure present at the inlet of the valve, said inlet being here connected to the mask 2. The cut off device 8 consists for example of an inflatable enclosure subjected to the pressure of the control inlet 6, or of a membrane whose face remote from the valve inlet is subjected to the pressure prevailing at the control inlet 6.

During the expiratory phases of the patient's breathing, the expiratory branch 4 communicates with the atmosphere on condition that the patient produces an expiratory pressure sufficient to open the expiration valve $V_E$, the control inlet 6 of which is then connected in a manner which will be explained below to a low pressure source 9. According to the preceding statements, if the relative pressure produced by the low pressure source 9 is zero, that is to say equal to atmospheric pressure, the expiration valve $V_E$ opens without the patient having to provide an expiratory pressure significantly greater than atmospheric pressure. On the contrary, if the relative pressure of the source 9 is greater than zero, the patient will himself have to provide a certain relative pressure in order to breathe out.

The inspiratory branch 3 of the patient circuit 1 is connected to the outlet of a pressurized inspiratory flow source 11 which can consist of a motor turbine group, an ejector or venturi assembly supplied by a compressor or a cylinder of compressed gas, etc.

Distribution means, comprising an inspiration valve $V_I$ arranged between the outlet of the inspiratory flow source and the inspiratory branch 3 of the patient circuit 1 control the gaseous exchanges as are initiated by the patient. According to the invention, the inspiration valve $V_I$ is driven by the electronic control device 12 in order to place the outlet of the inspiratory flow source in communication with the inspiratory branch 3 during the inspiratory phases of the patient's breathing, and to interrupt this communication during the expiratory phases.

The inspiratory flow source 11 is of a type capable of cancelling its flow with only a slight increase in pressure when its outlet is blocked. Thus, it is not necessary to modify the controls applied to the inspiratory flow source 11 according to whether the inspiration gate valve $V_I$ is open or closed. If the inspiratory flow source is a motor turbine group, its characteristics can be the following:

delivery pressure at maximum speed: 45 cm $H_2O$ (4.5 kPa), flow at maximum speed and zero outlet pressure: 280 to 300 l/mn.

With a view to safety, there is provided downstream from the inspiration valve $V_I$ a non-return flap valve 13 which causes the inspiratory branch 3 to communicate with the atmosphere when the pressure in the inspiratory branch 3 becomes less than the atmospheric pressure. Thus, the patient would not be deprived of fresh air should a breakdown keep the inspiration valve $V_I$ in the closed position.

The electronic control device 12 drives a control gate valve VC1 in synchronism with the inspiration valve $V_I$. The control gate valve VC1, of the three-way type, is installed in the control circuit 7 of the expiration valve $V_E$. When the inspiration valve $V_I$ is closed, the control gate valve VC1 connects the control inlet 6 of the expiration valve $V_E$ to the low pressure source 9. When valve $V_I$ is open, control gate valve VC1 connects the control inlet 6 to the outlet of the pressurized inspiratory flow source 11.

The low pressure source 9 consists of a link 14 between a second flow source 16 and an exhaust nozzle 17 to the atmosphere. The second flow source is adjustable in a range starting at zero value. In this case, the pressure in the link 14 is made equal to the atmospheric pressure through the nozzle 17 and as a result, in expiration phase, the pressure imposed on the patient is also the atmospheric pressure. On the contrary, if the flow rate of the second source 16 is not zero, a certain pressure, which is a function of this flow rate, establishes itself in the link 14 and consequently imposes a positive expiratory pressure on the patient. The pressures produced by the low pressure source 9 are lower than the pressure produced by the inspiratory flow source 11.

When the inspiration valve $V_I$ is open, the control gate valve VC1 connects the control inlet 6 of the expiration valve $V_E$ by means of a duct 10 to the pressure of the inspiratory flow source upstream from the inspiration valve $V_I$. Taking into account what was said above concerning the operation of the expiration valve $V_E$, such a pressure brings about the closure of the expiration valve $V_E$ and as a result the mask 2 is connected in a tight manner to the outlet of the inspiratory flow source.

In order to ensure the transition from the expiratory mode to the inspiratory mode and vice versa, the electronic control device 12 receives measurement signals produced by a flowmeter 18 and a manometer 19 supplying flow rate D and pressure P data of the flow through the inspiratory branch 3.

Some particular operational and automation features of FIG. 1 will now be described in more detail, with reference to FIG. 2.

When a test 21 detects that the inspiration gate valve $V_I$ is open, monitoring is carried out, in a part 22 of the organigram, of the pattern of the inspiratory flow rate. It is known that the inspiratory flow rate rapidly reaches a maximum $D_{MAX}$ at the beginning of each inspiratory phase. By means of the test 23 and step 24, the maximum flow rate value $D_{MAX}$ is updated afresh as long as the flow rate increases.

On the contrary, when the inspiratory flow rate starts to diminish, a test 26 is conducted which determines whether the instantaneous flow rate D has or has not become smaller than a certain fraction (coefficient K equal for example to 0.6) of the maximum flow rate $D_{MAX}$. If it has, the electronic control device 12 decides that the inspiratory phase is finished and it orders the closure of the inspiration valve $V_I$ and the actuation of the control gate valve VC1 in order to connect it to the low pressure source 9. If the response to the test 26 is negative, a test 28 is also conducted to check whether the duration of the inspiration does not exceed a maximum duration $T_{MAX}$, fixed arbitrarily for example at 3 seconds. If it does, an end of inspiration phase decision is also taken by step 27.

It is then again necessary to enter the test for the state of the inspiration valve $V_I$.

When this inspiration valve is closed, monitoring is carried out by a test 29 of the appearance, in the diagram showing pressure in relation to time, of a differential or drop $(P_2-P_1)/(T_2-T_1)$ which is smaller than a predetermined negative value A. In fact, a drop in pressure at the end of an expiration phase is indicative of a call for air on the part of the patient. If such a negative drop is detected, a test 31 on a logic parameter Q permits one to know whether it is a matter of the first iteration where the negative drop is detected during this expiratory cycle. If it is, the logic parameter Q is set at 1, by a step 32, and the moment $T_2$ of commencement of the drop below A is recorded on the register $T_A$. In the following iterations (negative output of the test 31), a test 33 will be used to seek the duration of this negative drop. When this duration becomes greater than a pre-established call period $D_A$, the electronic device decides on the end of the expiration period, that is to say the opening of the inspiration valve $V_I$ and the actuation of the control gate valve $VC_1$ in order to connect the control inlet 6 of the expiration valve $V_E$ to the outlet of the inspiratory flow source 11.

As long as the output of the test 29 or the output of the test 33 is negative, a test 34 is used to monitor the pattern of the time $T_{INS}$ which has elapsed since the beginning of the previous inspiration phase. If this duration becomes greater than a predetermined maximum respiratory period $T_F$, the electronic control device passes to the end of expiration step 36.

According to a variant represented by dotted lines in FIG. 1, the second flow source 16 can be materialized by a calibrated duct 15 connecting the link 14 to the outlet of the inspiratory flow source. In order to vary the flow rate through the duct 15, the calibration can be carried out by an adjustable cock up to a position of total closure. Even in this embodiment, the low pressure source is said to be "independent" or "separated" from the inspiratory flow source, in the sense that the pressure of the low pressure source, and consequently the low pressure signal applied to the control inlet 6 of the expiration valve $V_E$, assume the value desired for expiration without the operation of the inspiratory flow source having to be modified for this purpose.

Figure 3:
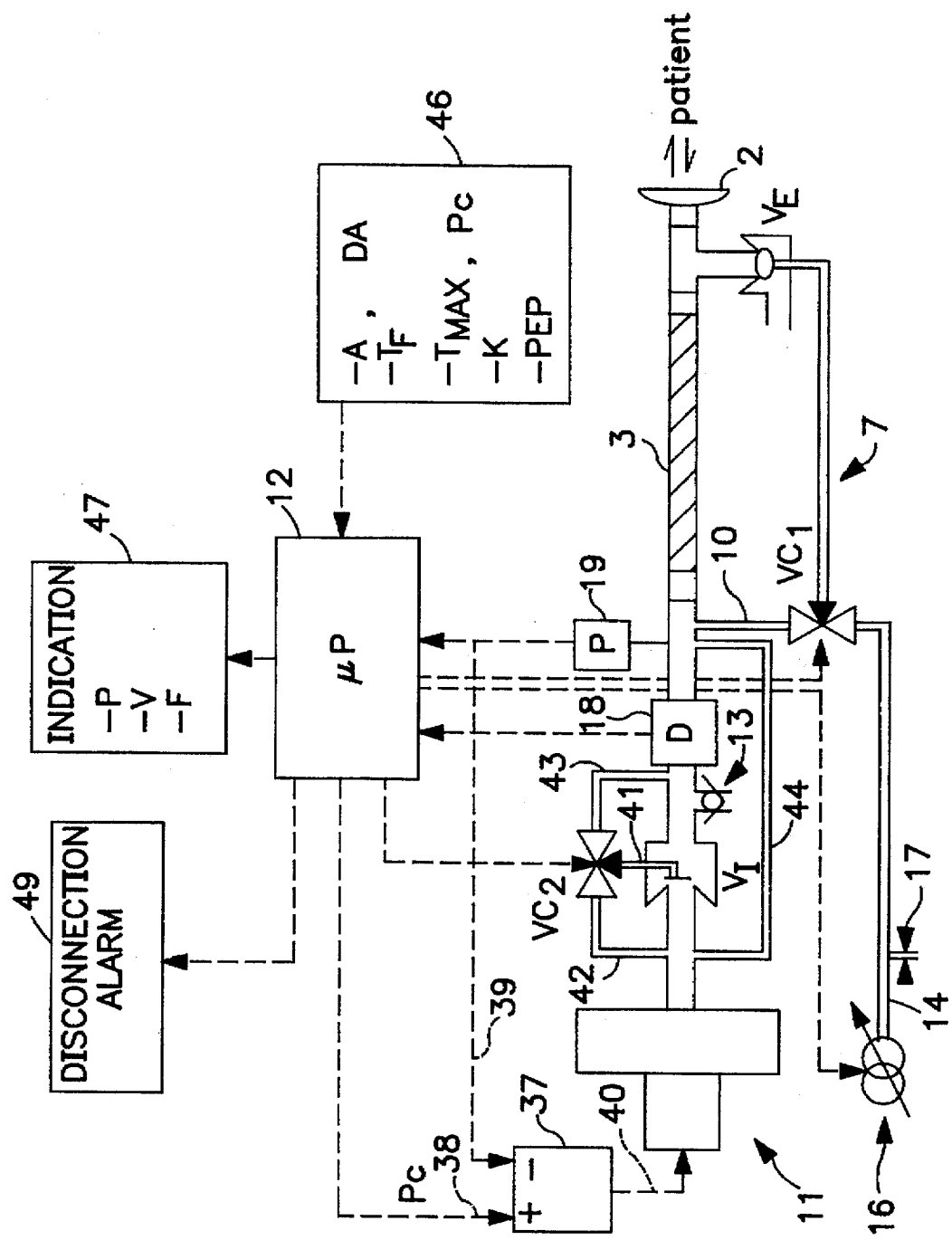
FIG. 3 is a diagram of a more particular embodiment of the device according to FIG. 1.

In the example represented in FIG. 3, the inspiratory flow source 11 consists of a motor turbine group supplied by a speed variator 37 receiving on its positive inlet 38 a pressure reference signal PC and on its negative inlet 39 a signal from the pressure detector 19. In relation to the difference between its two inputs 38 and 39, the speed variator 37 delivers a suitable power signal to the motor turbine group 11 on its outlet 40 in order to aim to restore the pressure P permanently to the reference value Pc during the inspiratory phases. In a manner which is not represented, during the expiratory phases, the variator 37 is short-circuited and the microprocessor sends to the motor turbine group a signal substantially maintaining the motor turbine group at the speed which it had during the previous inspiration.

The inspiration valve $V_I$ consists of a pneumatically controlled valve having a structure that may be similar to the expiration valve $V_E$. In particular, the valve $V_I$ has a control inlet 41 which is subjected in service to a pressure which determines the open or closed state of the valve.

The inspiration valve $V_I$ is linked to a control gate valve $VC_2$ which is of the three-way type in order to selectively connect the control inlet 41 to a duct 42 connected to the outlet of the motor turbine group 11 in order to realize the closure of the inspiration valve, or to a duct 43 connected to the inspirable gas path downstream from the valve $V_I$ in order to realize the open state of the inspiration valve $V_I$. It is understood that the pressure downstream from the inspiration valve $V_I$ necessarily establishes itself at an equilibrium value permitting the opening of the valve since, if the valve closed, the relative downstream pressure would disappear and as a result the valve would reopen straight away in a significant manner.

The inspiration valve $V_I$, the safety flap valve 13, the connection of the duct 43 to the principal inspiration path and the flowmeter 18 are moreover short-circuited by a leak compensation path 44 connecting the outlet of the motor turbine group 11 to the inspiratory branch 3. The function of this duct 44 is to compensate for the leaks that could exist for example between the mask 2 and the face of the patient during the expiratory phase. Such a leak can in fact prevent the maintenance of the positive expiratory pressure possibly imposed by the second flow source 16.

The second flow source 16 consists of a variable-flow compressor, controlled according to an instruction applied by the electronic control device 12, itself realized in the form of a microprocessor.

Moreover, in the example of FIG. 3, the duct 10 is connected to the inlet of the inspiratory branch 3, that is to say, in particular, downstream from the inspiration valve $V_I$ and the flowmeter 8.

Figure 2:
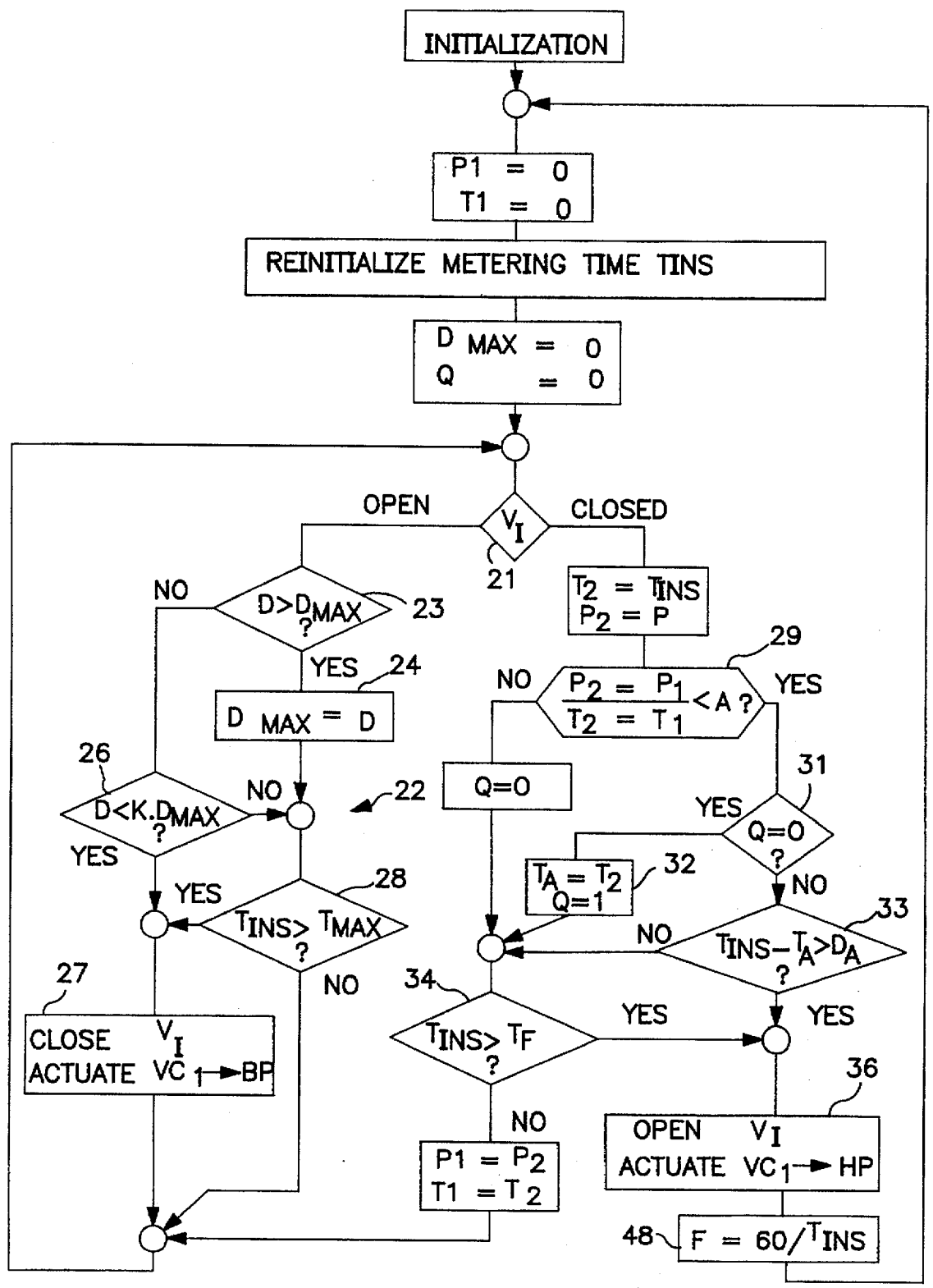
FIG. 2 is a control organigram of the device in FIG. 1.

The microprocessor 12 receives as input, for example by means of a keyboard not represented, various adjustments 46 relating in particular to the parameters A, DA, $T_F$, $T_{MAX}$, K, appearing in the organigram of FIG. 2, as well as the parameter PC representing the pressure condition applied to the inlet 38 of the speed variator 37, and the positive expiratory pressure PEP, serving to control the compressor 16.

The microprocessor 12 controls a display device 47 permitting indication of the pressure P measured by the sensor 19, the volume V of each inspiration, calculated by the microprocessor according to the signals supplied by the manometer 19 and the flowmeter 18, and the respiratory frequency F calculated at step 48, in cycles per minute, in FIG. 2.

If the flow rate read by the flowmeter preserves a maximum value for a predetermined duration, this is detected by the microprocessor 12 which actuates a disconnection alarm 49, sound and/or visual, to signal that an incident of the kind of a disconnection of the mask 2 has occured.

Figure 4:
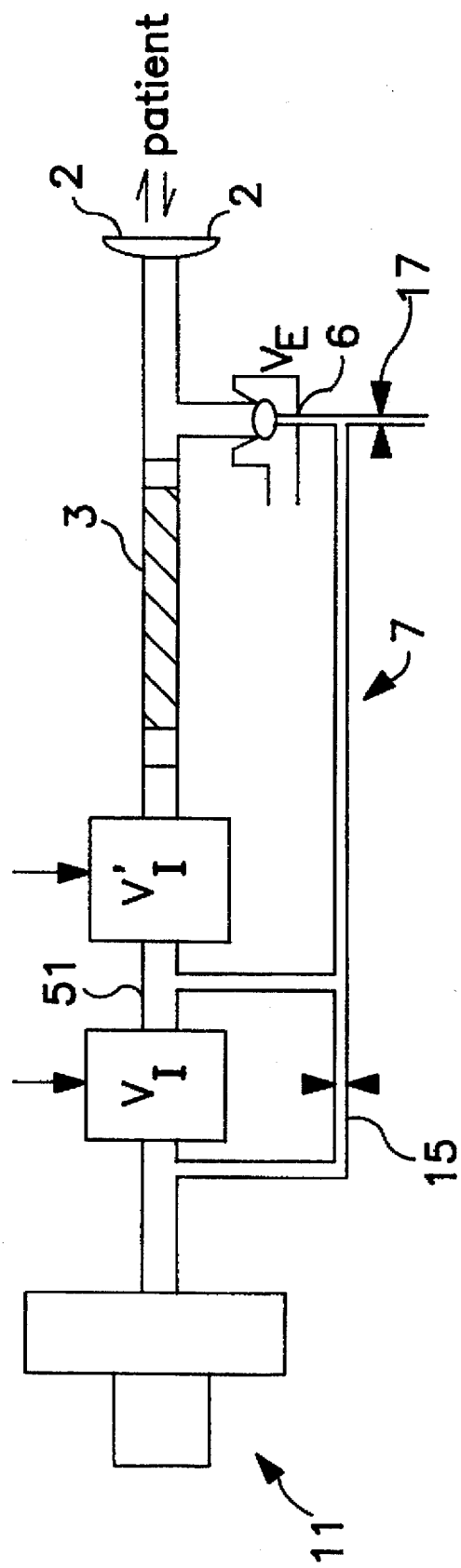
FIG. 4 is a simplified diagram relating to a variant.

In the example represented in FIG. 4, which will be described only as regards its differences compared with that of FIG. 1, inspiration valve $V_I$ is followed by a second inspiration valve $V'_I$ which can be opened and closed at the same time as valve $V_I$, or which can also consist of a non-return flap valve preventing the gas from passing from the inspiratory branch 3 towards the motor turbine group 11. The control inlet 6 of expiration valve $V_E$ is connected on the one hand directly to a calibrated exhaust orifice 17, on the other hand to the part 51 of the inspiratory path situated between the two inspiration valves $V_I$ and $V'_I$. The control inlet 6 is also directly connected to the low pressure source, here consisting of a calibrated link 15 with the outlet of the motor turbine group 11.

The operation is as follows:

When the two inspiration valves $V_I$ and $V'_I$ are open, the control inlet 6 of the expiration valve 2 is subjected to the inspiratory pressure supplied by the motor turbine group 11 thanks to the link with the part 51 of the inspiratory path. The valve $V_E$ is thus closed and the calibrated orifice 17 maintains the pressure difference between the inspiratory pressure and the atmospheric pressure.

For the expiration, the two valves $V_I$ and $V'_I$ are closed, and the control inlet 6 is subjected to the pressure defined by the link 15, or, if the link 15 is closed by an adjustment, to the atmospheric pressure through the calibrated orifice 17. The patient thus breathes out under the pressure determined in this way through the expiration valve $V_E$.

Figure 5:
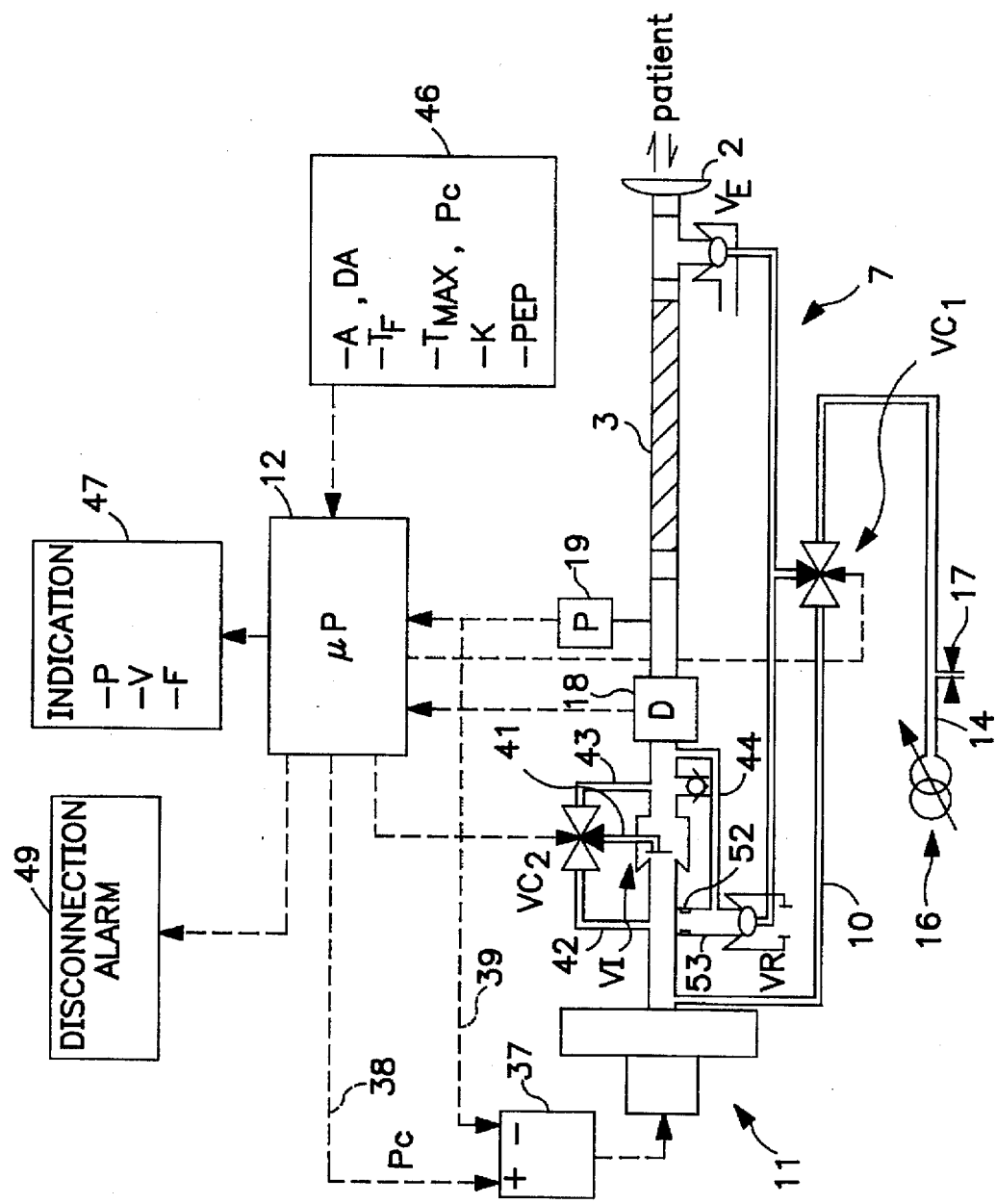
FIG. 5 is a diagram analogous to FIG. 3, but relating to a variant.

The device of FIG. 5 will be described only as regards its differences compared with that of FIG. 3. It comprises a supplementary valve $V_R$, connecting the outlet of the motor turbine group to the atmosphere and controlled by the control circuit 7 of the expiratory valve $V_E$ and thus by the same electric gate valve VC1 as the expiratory valve $V_E$. A restriction 52 is placed in a loop 53 connecting the outlet of motor turbine group 11 to the supplementary gate valve $V_R$.

The leak compensation circuit 44 is connected on one side between the valve $V_R$ and restriction 52, and on the other side, downstream from the inspiratory valve $V_I$.

The operation is as follows:

during inspiration, valve VR is closed, as it is controlled like VE.

during expiration, valve VR maintains upstream from itself a pressure equal to the expiration pressure PEP, as it is controlled like the valve VE by the mini-compressor 16.

There is a flow which goes to the atmosphere through the valve VR, as the pressure at the outlet of the motor turbine group 11 is greater than the expiration pressure PEP. This flow serves to cool the motor turbine group. There is also a flow which enters the patient circuit when the pressure in the latter is less than the expiration pressure PEP, that is to say in the case of a leak.

Contrary to the device in FIG. 3, the leak compensation flow is no longer permanent, but operates only when there is a leak.

The restriction 52 permits the maintenance of a significant pressure at the outlet of the motor turbine group (close to the inspiratory aid pressure) necessary for the closure of the inspiratory valve VI, and the limitation of the cooling flow rate in order that the supplementary valve VR can adjust the pressure upstream from itself.

Thanks to the invention, a simple, light apparatus is provided which does not require gas cylinders and permits use at home in a very broad range of pathological cases.

Naturally, the invention is not limited to the examples described and presented.

For example, in FIG. 3, instead of connecting the duct 43 which controls the opening of the inspiration valve $V_I$ to the inspiratory gas path, it could be connected to the low pressure defined by the low pressure source 14.

In the examples, the terms "valve" and "gate valve" are suitable for defining the elements $V_E$ and $V_I$, and $V_{C1}$ and $V_{C2}$ respectively. However, these terms need not be interpreted limitatively, and the "valve" $V_I$ in particular can be realized in the form of a mechanically or electromechanically controlled gate valve.

The expiration valve $V_E$ could be of a type other than pneumatically controlled, for example electrically controlled.

I claim:

1. Breathing aid device of the type with inspiration under substantially constant pressure, comprising a patient circuit (1) having an inspiratory branch (11) connected to a pressurized inspiratory flow source (3) and an expiratory branch (4) in which is installed an expiration valve ($V_E$) which is controlled so as to be closed during inspiration, the device also comprising electronic control (12) connected to at least one sensor (18, 19) detecting the respiratory activity of the patient and distribution means ($V_I$) which in inspiratory phase establish the communication between the inspiratory flow source (11) and the inspiratory branch (3) of the patient circuit, and in expiratory phase interrupt this communication at least partially, characterized in that the distribution means ($V_I$) are controlled by the driving means (12), which control the interruption of the said communication when the sensor detects that the patient is preparing an expiratory phase, and in that the driving means (12) also control, at least indirectly, the expiration valve ($V_E$) in order that it determines a predefined expiratory pressure substantially independent of the operating state of the inspiratory flow source (11).

2. The device according to claim 1 comprising an inspiratory control adapted to maintain said inspiratory pressure during said expiration.

3. The device according to claim 1 wherein said inspiratory control is adapted to adjust said pressurized source to provide a substantially equal pressure during said inspiration and said expiration.

4. A breathing aid device for a patient adapted to provide inspiration under substantially constant inspiratory pressure, said device comprising a patient circuit (1) having an inspiratory branch (3) connected to an outlet of a pressurized inspiratory flow source (11) and an expiratory branch (4), a sensor control connected to at least one sensor which is adapted to detect respiratory activity of said patient, a distribution element ($V_I$) controlled by said sensor control to establish communication between said pressurized source (11) and said inspiratory branch (3) during inspiration by said patient and having means to at least partially interrupt said communication when said patient is about to begin expiration, and an expiration valve 617 ($V_E$) in said expiration branch controlled by said sensor control to be closed during said inspiration and having means to determine, during said expiration, a predefined expiratory pressure substantially independently of said said pressurized source (11).

5. Device according to claim 4, characterized in that the inspiratory flow source is a motor turbine group (11).

6. The device according to claim 4 characterized in that said distribution element comprises a pneumatically controlled inspiration valve ($V_I$), and a control inlet (41) connected selectively to said outlet of said pressurized source (11) during said expiration and to a lower pressure (43) during said inspiration.

7. The device according to claim 6 wherein, during said inspiration, said control inlet (41) is connected to said inspiration branch (3).

8. The device according to claim 4 wherein said distribution element ($V_I$) is adapted to allow a leak compensation flow (44) between said pressurized source (11) and said patient circuit (1) during said expiration.

9. The device according to claim 4 wherein said distribution element ($V_I$) is by-passed by a loop (53,54) having a restriction (52) and, downstream from said restriction, also has a supplementary gate valve (VR) controlled to be closed during said inspiration to maintain in said loop (53,54) and downstream from said restriction (52), during expiration, a pressure close to said predefined expiratory pressure (PEP).

10. The device according to claim 4 wherein an expiration control actuates a connection (7,VC1) between a control inlet (6) of said expiration valve ($V_E$) and a low pressure source (9,15) to pneumatically control expiration valve ($V_E$).

11. The device according to claim 10 wherein said connection comprises a gate (VC1) in a control circuit (7) of said expiration valve ($V_E$), said gate controlled by control (12) to connect said control inlet (6) of said expiration valve to said low pressure source (14) during said expiration.

12. The device according to claim 11 wherein said gate comprises a three-way gate valve (VC1) selectively connecting said control inlet (6) of said expiration valve ($V_E$) to said pressurized source (11) and to said low pressure source (14).

13. The device according to claim 10 wherein said low pressure source comprises a link between an exhaust nozzle (17) and an outlet of a second flow source (16).

14. The device according to claim 13 wherein said second flow source comprises a compressor (16).

15. The device according to claim 13 wherein said second flow source comprises a device (15) linking with the said pressurized source (11).

16. The device according to claim 4 wherein said predefined expiratory pressure is adjustable and can assume a value at least equal to atmospheric pressure.

17. The device according to claim 4 wherein control (12) controls the closure of said expiration valve ($V_E$) when the pressure in the patient circuit falls at the end of said expiration.

18. The device according to claim 17 wherein said control (12) is responsive to variation in pressure in said patient circuit in relation to time.

19. The device according to claim 4 comprising sensors (18, 19) for measuring the pressure (P) and the flow rate (D) in said inspiratory branch (3) of said patient circuit, and a device for determining a variable indicative of a volume of inspired gas.

20. The device according to claim 4 comprising an actuator for a disconnection alarm if the flow rate remains high in said inspiratory branch (4) for a predetermined period.

21. A breathing aid device for a patient of the type with inspiration under substantially constant inspiration pressure comprising a patient circuit (1) having an inspiratory branch (3) connected to a pressurized inspiratory flow source (11) and an expiratory branch (4), a sensor control (12) connected to at least one sensor (18, 19) which is adapted to detect respiratory activity of said patient, a distribution element ($V_I$) controlled by said sensor control to establish communication between said inspiratory flow source (11) and said inspiratory branch (3) of the patient circuit during inspiration phase and to interrupt said communication at least partially when said patient is about to begin said expiration, and an expiration valve ($V_E$) mounted in said expiratory branch and at least indirectly controlled by said sensor control to be closed during inspiration and to determine during expiration a predefined expiratory pressure substantially independent of the operating state of the inspiratory flow source (11), wherein said distribution element comprises a pneumatically controlled inspiration valve, a control inlet which is connected selectively to the outlet of the inspiratory flow source during expiration and to a lower pressure during inspiration.

22. The device according to claim 21 wherein the inspiratory flow source is a motor turbine group.

23. The device according to claim 21 comprising an inspiratory flow source control which is operative for keeping the inspiratory flow source in pressure delivering operation during the expiratory phase.

24. The device according to claim 21 wherein the inspiratory control comprises a device for adjusting the inspiratory flow source to provide a substantially equal outlet pressure during inspiration and expiration.

25. The device according to claim 21 wherein during inspiration said control inlet (41) is connected to a flow path between the inspiration valve ($V_I$) and the patient circuit (1).

26. The device according to claim 21 wherein the distribution element is adapted to allow a leak compensation flow (44) between the inspiratory flow source (11) and the patient circuit (1) during expiration.

27. The device according to claim 21 wherein the distribution element ($V_I$) is by-passed by a loop (53,54) fitted with a restriction (52) and, downstream from this restriction, is provided with a supplementary gate valve (VR) adapted to be closed during inspiration to maintain in said loop and downstream from said restriction (52), during expiration, a pressure close to the predefined expiratory pressure (PEP).

28. The device according to claim 21 wherein the expiration valve ($V_E$) is pneumatically controlled, and wherein, to control the expiration valve ($V_E$), an expiration control controls actuation of a connection (7, VC1) between a control inlet (6) of the expiration valve ($V_E$) and a low pressure source (9,15).

29. The device according to claim 28 wherein the connection comprises a gate (VC1) in a control circuit (7) of the expiration valve ($V_E$) and controlled by the expiration control (12) to connect the control inlet (6) of the expiration valve to the low pressure source (14) when the patient is breathing out.

30. The device according to claim 29 wherein the gate comprises a three-way gate valve (VC1) selectively connecting the control inlet (6) of the expiration valve ($V_F$) to the pressurized flow source (11) and to the low pressure source (14).

31. The device according to claim 28 wherein the low pressure source comprises a link (14) between an exhaust nozzle (17) and an outlet of a second flow source (16).

32. The device according to claim 31 wherein the second flow source comprises a compressor (16).

33. The device according to claim 31 wherein the second flow source comprises a device (15) linking with the inspiratory flow source (11).

34. The device according to claim 21 wherein the predefined expiratory pressure is adjustable and can assume a value at least equal to atmospheric pressure.

35. The device according to claim 21 wherein the expiration control (12) controls closure of the expiration valve ($V_E$) when pressure in the patient circuit falls at the end of said expiration.

36. The device according to claim 35 wherein the expiration control (12) is responsive to variations in pressure in the patient circuit over time.

37. The device according to claim 21 comprising a device (18, 19) for measuring pressure (P) and flow rate (D) in the inspiratory branch (3) of the patient circuit, and a calculation for determining variable indicative of the volume of inspired gas.

38. The device according to claim 21 having means for an actuator for setting off a disconnection alarm if the flow rate remains high in the inspiratory branch (4) for a predetermined period.

39. A breathing aid device for a patient of the type with inspiration under substantially constant inspiration pressure comprising a patient circuit (1) having an inspiratory branch (3) connected to a pressurized inspiratory flow source (11) and an expiratory branch (4), a sensor control (12) connected to at least one sensor (18, 19) which is adapted to detect respiratory activity of the patient, a distribution element ($V_1$) controlled by said sensor control to establish communication between the inspiratory flow source (11) and the inspiratory branch (3) of the patient circuit during inspiration and to interrupt this communication at least partially, when said patient is about to begin said expiration, and an expiration valve ($V_E$) mounted in said expiratory branch and at least indirectly controlled by said sensor control to be closed during inspiration and to determine during expiration a predefined expiratory pressure substantially independent of the operating state of the inspiratory flow source (11), wherein said distribution element is by-passed by a loop (53, 54) having a restriction (52) and, downstream from this restriction, having a supplementary gate valve (VR) adapted to be closed during inspiration and to maintain in said loop and downstream from said restriction (52), during expiration, a pressure close to the predefined expiratory pressure (PEP).

40. The device according to claim 39 wherein the inspiratory flow source is a motor turbine group.

41. The device according to claim 39 comprising inspiratory flow source control means which are operative for keeping the inspiratory flow source in pressure-delivering operation during the expiratory phase.

42. The device according to claim 39 wherein the inspiratory control comprises a device for adjusting the inspiratory flow source to provide a substantially equal outlet pressure during inspiration phases and expiration.

43. The device according to claim 39 wherein the distribution element is adapted to allow a leak compensation flow (44) between the inspiratory flow source (11) and the patient circuit (1) during expiration.

44. The device according to claim 39 wherein the expiration valve ($V_E$) is pneumatically controlled and wherein, to control the expiration valve ($V_E$) an expiration control actuator of a connection (7, VC1) between a control inlet (6) of the expiration valve ($V_E$) and a low pressure source (9,15).

45. The device according to claim 44 wherein the connection comprises a gate (VC1) in a control circuit (7) of the expiration valve ($V_E$) and controlled by expiration control (12) to connect the control inlet (6) of the expiration valve to the low pressure source (14) when the patient is breathing out.

46. The device according to claim 45 wherein a gate comprises a three-way gate valve (VC1) selectively connecting the control inlet (6) of the expiration valve ($V_E$) to the pressurized flow source (11) and to the low pressure source (14).

47. The device according to claim 39 wherein the low pressure source comprises a link (14) between an exhaust nozzle (17) and an outlet of a second flow source (16).

48. The device according to claim 47 wherein the second flow source comprises a compressor (16).

49. The device according to claim 47 wherein the second flow source comprises a device (15) linking with the inspiratory flow source (11).

50. The device according to claim 39 wherein the predefined expiratory pressure is adjustable and can assume a value at least equal to atmospheric pressure.

51. The device according to claim 39 wherein the expiration control (12) controls closure of the expiration valve ($V_E$) when pressure in the patient circuit falls at the end of said expiration.

52. The device according to claim 51 wherein expiration control (12) is responsive to variations in pressure in the patient circuit over time.

53. The device according to claim 39 comprising a device (18, 19) for measuring pressure (P) and flow rate (D) in the inspiratory branch (3) of the patient circuit, and means for calculating a variable indicative of the volume of inspired gas.

54. The device according to claim 39 having means for an actuator for setting off a disconnection alarm if the flow rate remains high in the inspiratory branch (4) for a predetermined period.

55. A breathing aid device for a patient of the type with inspiration under substantially constant inspiration pressure, comprising a patient circuit (1) having an inspiratory branch (11) connected to a pressurized inspiratory flow source (3) and an expiratory branch (4), a sensor control (12) connected to at least one sensor (18, 19) which is adapted to detect respiratory activity of the patient, a distribution element ($V_I$) controlled by said sensor control to establish communication between the inspiratory flow source (11) and the inspiratory branch (3) of the patient circuit during inspiration and to interrupt this communication at least partially, when said patient is about to begin said expiration, and a pneumatically controlled expiration valve ($V_E$) mounted in said expiratory branch and at least indirectly controlled by said sensor control to be closed during inspiration and to determine during expiration a predefined expiratory pressure substantially independent of the operating state of the inspiratory flow source (11), wherein to control the expiration valve ($V_E$), the sensor control controls a three-way gate valve (VC1) installed in a control circuit (7) of the expiration valve ($V_E$) to connect a control inlet (6) of the expiration valve to a low pressure source (14) when the patient is breathing out, and to the pressurized flow source (11) when the patient is breathing in.

56. The device according to claim 55 wherein the inspiratory flow source is a motor turbine group.

57. The device according to claim 55 comprising inspiratory flow source control means which are operative for keeping the inspiratory flow source in pressure-delivering operation during the expiratory phase.

58. The device according to claim 55 wherein the inspiratory control comprises a device for adjusting the inspiratory flow source to provide a substantially equal outlet pressure during inspiration and expiration.

59. The device according to claim 55 wherein the distribution element is adapted to allow a leak compensation flow (44) between the inspiratory flow source (11) and the patient circuit (1) during expiration.

60. The device according to claim 55 wherein the distribution element ($V_I$) is by-passed by a loop (53, 54) fitted with a restriction (52) and, downstream from this restriction, having a supplementary gate valve (VR) adapted to be closed during inspiration and to maintain in said loop and downstream from said restriction (52), during expiration, a pressure close to the predefined expiratory pressure (PEP).

61. The device according to claim 55 wherein the low pressure source comprises a link (14) between an exhaust nozzle (17) and an outlet of a second flow source (16).

62. The device according to claim 61 wherein the second flow source comprises a compressor (16).

63. The device according to claim 61 wherein the second flow source comprises a device (15) linking with the inspiratory flow source (11).

64. The device according to claim 55 wherein the predefined expiratory pressure is adjustable and can assume a value equal to the atmospheric pressure.

65. The device according to claim 55 wherein inspiration control (12) controls the closure of the expiration valve ($V_E$) when the pressure in the patient circuit falls at the end of the patient's expiration phase.

66. The device according to claim 65 wherein the inspiration control (12) is responsive to variations in pressure in the patient circuit in relation to time.

67. The device according to claim 55 comprising a device (18, 19) for measuring pressure (P) and flow rate (D) in the inspiratory branch (3) of the patient circuit, and a calculation for determining variable indicative of the volume of inspired gas.

68. The device according to claim 55 having an actuator for setting off a disconnection alarm if the flow rate remains high in the inspiration branch (4) for a predetermined period.

* * * * *

UNITED STATES PATENT AND TRADEMARK OFFICE
CERTIFICATE OF CORRECTION

PATENT NO. : 5,664,562
DATED : Sep. 9, 1997
INVENTOR(S) : Guy Bourdon

It is certified that error appears in the above-identified patent and that said Letters Patent is hereby corrected as shown below:

Column 7, Line 32, change "valve 2", to read --$V_E$--.

Signed and Sealed this

Fourteenth Day of July, 1998

Attest:

BRUCE LEHMAN

*Attesting Officer*    *Commissioner of Patents and Trademarks*

UNITED STATES PATENT AND TRADEMARK OFFICE
CERTIFICATE OF CORRECTION

PATENT NO. : 5,664,562
DATED : Sep. 9, 1997
INVENTOR(S) : Guy Bourdon

It is certified that error appears in the above-identified patent and that said Letters Patent is hereby corrected as shown below:

On the title page, item [73], under Assignee: change "Pierre Medical S.A., France", to read --Nellcor Puritan Bennett France Developpement--.

Signed and Sealed this

Twenty-ninth Day of June, 1999

Attest:

Q. TODD DICKINSON

Attesting Officer     Acting Commissioner of Patents and Trademarks